United States Patent [19]
Din

[11] Patent Number: 5,035,615
[45] Date of Patent: Jul. 30, 1991

[54] DENTAL FILLING BAND AND METHOD OF USE

[76] Inventor: Franklin Din, 33 State Rd., Princeton, N.J. 08540

[21] Appl. No.: 531,299

[22] Filed: May 31, 1990

[51] Int. Cl.$^5$ .............................. A61C 5/04; A61C 5/00
[52] U.S. Cl. ...................................... 433/39; 433/215; 433/226
[58] Field of Search ................... 433/39, 40, 215, 229, 433/226, 227, 228

[56] References Cited

U.S. PATENT DOCUMENTS

| | | | |
|---|---|---|---|
| 4,514,174 | 4/1985 | Dougherty et al. | 433/226 |
| 4,563,152 | 1/1986 | McClure | 435/39 |
| 4,778,385 | 10/1988 | Herrin | 433/40 |
| 4,797,431 | 1/1989 | Billington et al. | 523/116 |

Primary Examiner—John J. Wilson
Assistant Examiner—Cindy A. Cherichetti
Attorney, Agent, or Firm—Mathews, Woodbridge & Collins

[57] ABSTRACT

A dental matrix band that is flexible and bondable to resin based restorative materials. This matrix band will permanently bond to the filling and the tooth. It becomes a permanent part of the composite restoration and may be wholly retained, partially retained, or completely removed depending upon the neeeds of the dentist, patient and the specific purpose for which this band is used. The dentist forms a prepared cavity. The thin, flexible composite matrix band is then inserted between the tooth and the adjacent tooth. The band is firmly held against the tooth with the surface of the band passively abutting the adjacent tooth. A bonding agent is applied to the appropriate tooth surfaces, the cavity and the band. The agent is cured, the prepared cavity is filled with a composite resin, the resin is cured and the excess portion of the band is removed.

10 Claims, 3 Drawing Sheets

DENTAL FILLING BAND AND METHOD OF USE

BACKGROUND OF THE INVENTION

1. Field of the Invention

This invention relates to dental restoration structures and methods, and, more specifically, to dental matrix bands that may be bonded to resin-based filling materials and methods of using the same.

2. Description of the Related Art

Composite dental resins have many advantages over other restorative materials such as amalgam, a popular restorative material. When compared to amalgam, such resins are superior in color, smoothness and bondability. It is also noted that amalgams, unlike resins, contain mercury, a substance considered by many to be objectionable. Although composite resins are finding greater use, they are not without their problems. These problems include the following: (a) there are a high percentage of "open contacts" associated with interproximal composite restorations; (b) composite restorations are difficult to trim and finish; and (c) uncured composite resins stick to metal instruments.

With respect to problem (a) above, "open contacts" are usually the result of the space occupied by the matrix band during the process of restoration. More specifically, once an interproximal cavity has been prepared, a matrix band is placed around the tooth. After the band is placed, a wedge is pushed between the outer surface of the band and the adjacent tooth. The wedge serves a number of purposes. First, the wedge tightly compresses the band against the cervical margin of the cavity, i.e. the margin closest to the root. Secondly, the wedge forces the adjacent teeth apart. In an ideal interproximal restoration, the adjacent teeth will move back toward each other after the wedge and band are removed such that the adjacent tooth and the filling will passively abut. If the filling does not abut the adjacent tooth, there is a gap between the teeth known as an "open contact".

Those concerned with the development of dental equipment and methods have long recognized the need for restorative procedures and structures that reduce the number of "open contacts". For example, U.S. Pat. No. 2,035,347 is directed to a filling method that employs a strip of metal having a plurality of different sized spheroidal projections that may be used as contact points to close "open contacts". In the '347 patent, that portion of the metal strip having the appropriate sized contact point is placed in position against the filling immediately after the matrix band is removed. According to the '347 patent, "the free mercury in the filling will immediately amalgamate the metal in the surface of the fillet", i.e. the metal strip will bond to the filling with the contact point in place to close the "open contact".

Another solution to the "open-contact" problem is proposed in U.S. Pat. No. 4,778,385. In this patent, a collection of different sized composite matrix structures having convex and concave surfaces are preformed and supplied to the dentist. A matrix, sized to cover the proximal cavity and close the "open contact", is chosen from the supply and firmly placed against the proximal surface of the tooth using a wedge. The tooth is then filled with a composite restorative material that has the identical composition as the material from which the composite matrix is made. The composite material and a bonding agent, previously applied to the proximal surface of the tooth and the inner surface of the matrix, are now cured. The wedge is then removed and the process is finished. In some cases shrinkage of the matrix occurs resulting in exposed margins. In those cases, bonding agent is applied to the exposed margins and cured.

Although these devices have served the purpose, they are subject to some serious limitations. Both the '347 and '385 patents teach devices that are preformed, pre-shaped and not flexible. Hence, both patents teach structures that must be supplied to the dentist in multiple sizes and shapes in order to be useful thereby making the devices expensive to manufacture, and cumbersome to store and use. Furthermore, the '385 patent teaches a structure that must be made of the identical material as the filling material, another serious limitation on its use.

The use of a wedge in the '385 patent is still a further limitation. Its use, like most conventional wedges, can cause numerous problems, such as bleeding from the gums and matrix band deformation, which increase the difficulties in achieving a successful composite restoration. Also, there is no way to accurately measure the amount of separation, if any, produced by a wedge. Misjudgments in wedge placement can, therefore, result in a contact that is either too tight or open after the wedge is removed. Shrinkage of a preformed matrix after curing the agent and filling is still a further serious shortcoming in trying to avoid an "open contact" with prior art devices.

With respect to the trimming and finishing problem (problem (b) above), composite restorations are more difficult to trim and finish than amalgams. Amalgams are soft and plastic when trimming and finishing are performed. With composite resins, there is no intermediary plastic state prior to hardening that allows easy trimming and finishing. As such, with resin-based restorations, the trimming and finishing process is tedious, delicate and time consuming. Therefore, those skilled in these arts have long sought devices and methods for use in resin-based restorations that reduce the amount of trimming and finishing necessary to complete a restoration.

Because of the sticking problem (problem (c) above), i.e. uncured composite resins stick to metal instruments, dentists are often required to have a second set of instruments for working with composite resins in addition to the standard metal instruments. For example, when performing the process disclosed in the '385 patent, the dentist should have a special instrument with a non-metal surface (e.g. teflon coated) for use in filling the void, i.e. during condensing of the composite restoration material in order to avoid sticking problems. Besides being expensive, the need for additional instruments makes the process more complicated to perform.

As such, present devices and methods for performing restorations with composite resins have problems that result in a number of serious limitations. The present invention mitigates these problems.

SUMMARY OF THE INVENTION

The general purpose of this invention is to provide dental restoration structures and processes which embrace all of the advantages of similarly employed devices and methods, and possess none of the aforedescribed disadvantages. To attain this, the present invention contemplates a unique dental matrix band for use in making better composite restorations with less trauma to the patient, less chair time per restoration, less post operative complications, and lower overall treatment costs. With the present invention, "open contacts" will occur less frequently. Also, trimming and finishing procedures will be less complicated and time consuming.

The present invention includes a dental matrix band that is generally formed in one standard size as a thin, flexible, elongated strip of material bondable to a variety of resin-based filling materials. When used for restorations, the band becomes a permanent, integral part of the filling. The band may be made of the same general size and shape as current non-bondable matrix bands (e.g. stainless steel and mylar). As such, this new matrix band may be used in a similar fashion to the conventional types, the major difference being that a portion of this band remains in place after the resin-based filling is cured. Hence, with this invention, there is no need for the dentist to learn radically different procedures and techniques. Also, under some circumstances, the free ends of a matrix band can be cut off by the dentist and the pieces used as an instrument to aid in condensing the occlusal portion of the filling. When the band is used in this manner, the dentist may use conventional metal-surfaced tools.

According to one aspect of this invention the dentist forms in a tooth a prepared cavity in a conventional manner. The thin, flexible composite matrix band is then placed around the tooth. The band is firmly held against the margins of the cavity while the outer surface of the band passively abuts the adjacent tooth. A bonding agent is then applied to the surface of the prepared cavity and to the inside surface of the band. During this step, the agent will cover those regions where the inside of the band and the tooth are in contact. These regions of contact often include the cavity margins or tooth surfaces adjacent thereto. The agent is then cured to hold the band in place. Next, the prepared cavity is filled with a composite resin, the resin is cured and the excess portion of the band is removed.

The exact nature of this invention as well as other objects and advantages thereof will be readily apparent from consideration of the following specification relating to the annexed drawings.

BRIEF DESCRIPTION OF THE DRAWINGS

FIGS. 7A–7G are views illustrating various method steps and wherein FIGS. 7A–7C and 7E–7G are pictorial views and FIG. 7D is a top view.

DETAILED DESCRIPTION OF THE PREFERRED EMBODIMENT

Figure 1:
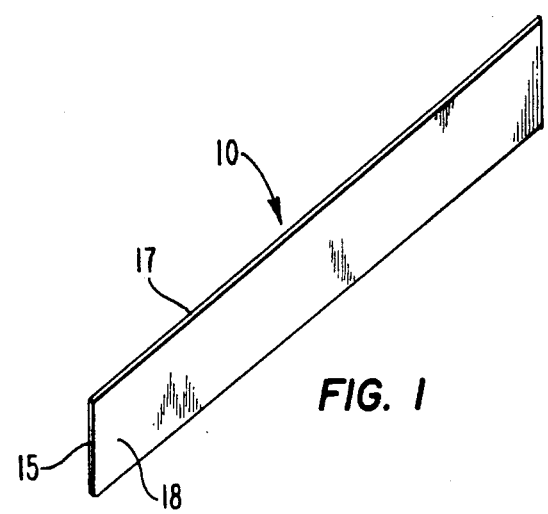
FIGS. 1 and 2 are pictorial views of the preferred embodiment of the invention.
Figure 2:
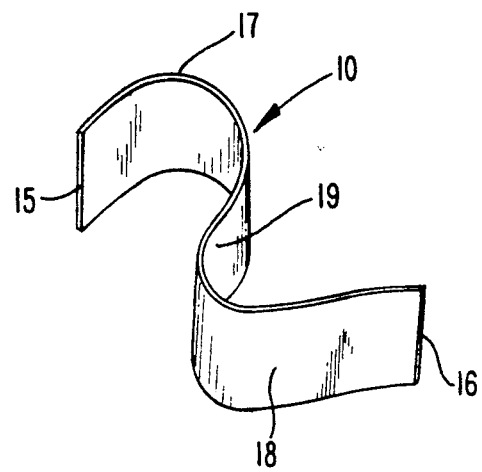

Referring now to the drawings, there is shown in FIGS. 1 and 2 a thin, flexible, ribbon-like matrix band 10 having opposed, broad rectangular faces 18, 19, a top edge 17, and opposed ends 16, 15. The band 10, preferably formed into the shape shown in FIG. 1, is sufficiently flexible to be bendable into a multitude of different shapes such as that shown in FIG. 2. For purposes of shipping and storage a plurality of bands 10 may be laid flat and stacked upon each other.

It is contemplated that the matrix band 10 be made of a material capable of being bonded to at least one, and preferably to a variety, if not all, of the many resin-base bonding liquids and resin-based filling materials commercially available.

In the preferred embodiment, the bondable matrix band 10 is composed of one of the conventional light-activated filler materials such as fluoroaluminosilicate glass powder, and one of the conventional light-cured liquid resins such as bisphenol glycidal methacrylate (BIS-GMA). In most cases, using the type of materials mentioned above, the weight-ratio of powder to liquid may fall in the range from 3.3:1 down to 0.5:1 for successful results. Bands 10 having excellent characteristics were produced from commercial materials using the weight-ratio of 1.6:1 for powder to liquid, respectively.

Using the particular ingredients mentioned above to form the band 10 also has the advantage that a variety of bonding agents and filling materials may be used during the restoration. For example, any one of the following bonding agents: Caulk's Universal Bond ®, Caulk's Universal Bond II ® and 3M's Scotch Bond II ®; and any one of the following filling materials: Kerr's Herculite XR ®, 3M's P-50 ® and Caulk's Prisma A.P.H. ® may be used in conjunction with a band 10 when it is formed from a mixture of fluoroaluminosilicate glass powder and BIS-GMA.

The band 10 may be formed by first mixing the powder and liquid, then drawing the mixture into the film and finally curing the film. The band 10 may be made into a variety of sizes. However, a band 10 having a length (edge 17) of 50 mm, a width (edge 16) of 10 mm and a thickness of 0.05 mm would probably be sufficient for most cases. The thickness of the band 10 should be carefully controlled so that the band 10 is sufficiently flexible to be properly wrapped around the tooth, while still maintaining sufficient structural rigidity so that it will not collapse of its own weight.

Since the band 10 is to become an integral part of the restored tooth, it should have a color compatible with tooth colored restoratives and have a smooth finish. To be mechanically workable, the band 10 must resist stretching, be thin and be easily cut. As such, the band 10 may be used in anterior as well as posterior restorations in all standard cavity classes I through V. The proposed formulation has these characteristics.

Figure 3:
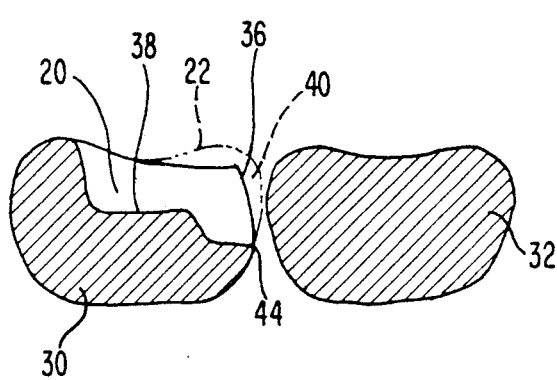
FIG. 3 is a sectional elevation of a pair of adjacent teeth to be restored with the structure and methods of the present invention.

FIGS. 3–6 illustrate the application of band 10 to a typical class II cavity preparation 20 in a posterior tooth 30. The interproximal contact has been lost between teeth 30 and 32, resulting in a gap 40 (FIG. 3). The tooth 30 must be restored to the desired shape 22 shown in phantom line.

Figure 4:
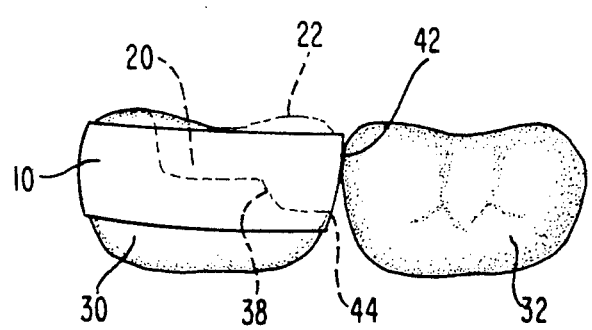
FIG. 4 is an elevational view showing the structure of FIG. 1 in combination with the teeth of FIG. 3.
Figure 5:
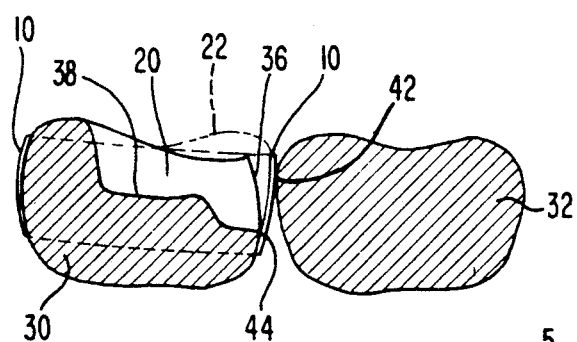
FIG. 5 is a sectional elevation taken along the line 5—5 of FIG. 6.
Figure 6:
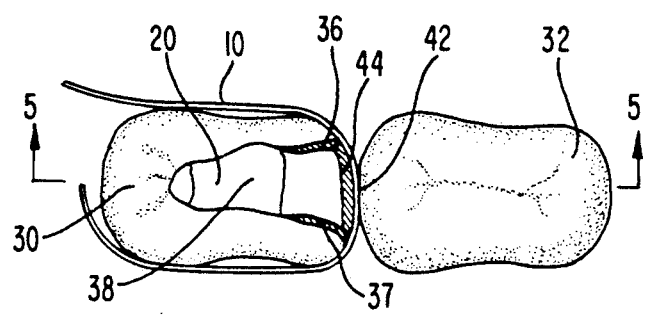
FIG. 6 is a top view of the structure shown in FIG. 4.

In FIGS. 4–6, the bondable matrix band 10 is placed around the tooth 30. The band 10 abuts the tooth 30 at or beyond the cervical margin 44 while passively abutting the contact area 42 of tooth 32. The band 10 also abuts tooth 30 at or near the vertical margins 36, 37 of the cavity preparation 20. The cavity preparation 20 includes an inner floor surface 38.

Figure 7A:
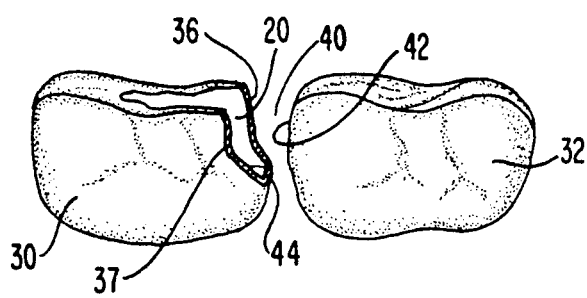

FIGS. 7A-7G illustrate the preferred method of executing a typical tooth restoration using the band 10 in the manner just described with respect to FIGS. 3-6. In FIG. 7A, the cavity preparation 20 is formed in the usual manner. The marginal edges 36, 37 and 44 of the cavity preparation 20 may be beveled by drilling and the appropriate surfaces are acid etched to provide a bonding surface to which the band 10 will eventually adhere.

Figure 7B:
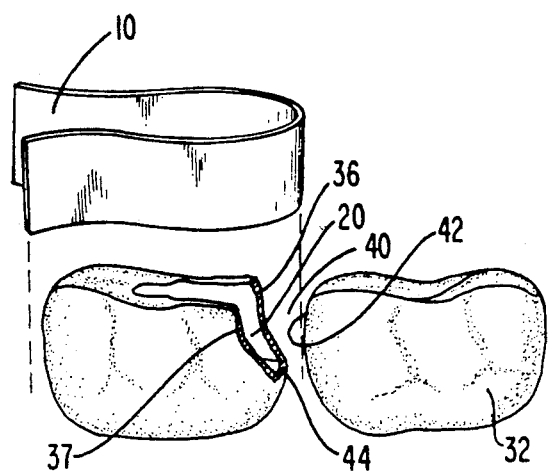
Figure 7C:
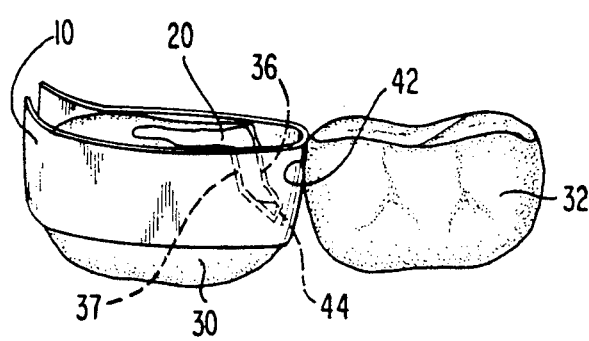

In FIGS. 7B and 7C, the band 10 is placed into the gap 40 and wrapped around the tooth 30. Using the dentist's hand, the band 10 is held against the tooth surface near the cervical margin 44 and the margins 36, 37. In doing this, the dentist will provide enough slack in the band 10 to permit it to passively touch the surface of tooth 32 at the contact area 42. At this point, the cavity preparation 20 is prepared to receive the bonding agent and the filling material.

Figure 7D:
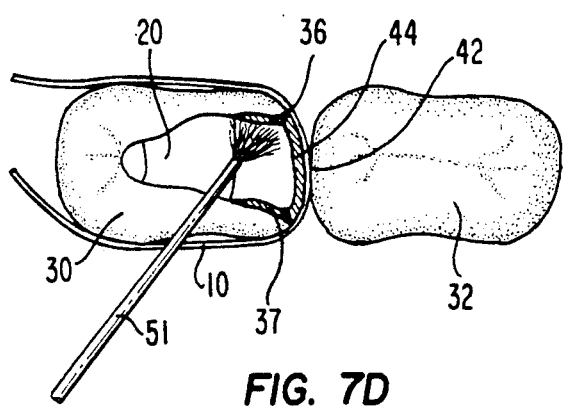
Figure 7E:
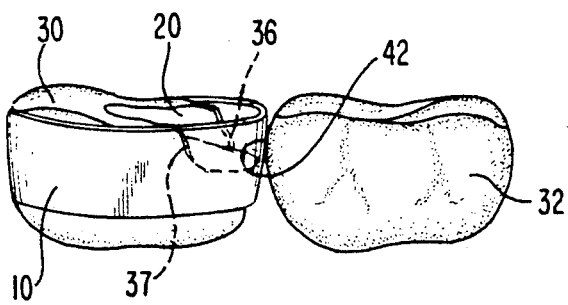
Figure 7F:
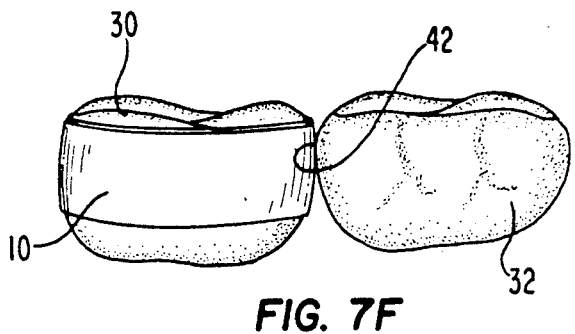
Figure 7G:
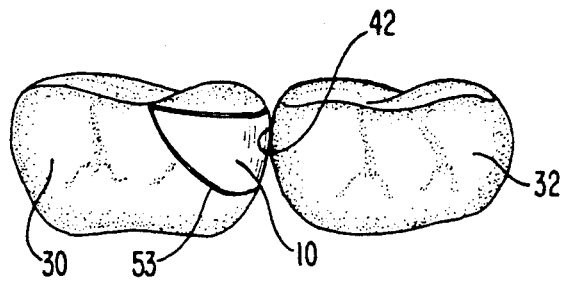

FIG. 7D illustrates the application of a liquid bonding agent with a brush 51 to the inner surface of cavity preparation 20, and the margins 36, 37 and 44, the inside surface of band 10 and the adjacent regions of the tooth 30 in contact with band 10. The bonding agent is then cured in an appropriate manner, i.e. the dentist either waits an appropriate time for chemical curing to take place or applies ultraviolet (UV) light or visible light radiation from an appropriate source to the bonding agent. After curing has taken place and with the band 10 now bonded to the tooth at or beyond the margins 36, 37 and 44, filling material is applied to the cavity preparation 20. When using light or UV-curable materials, the filling material is often applied in several steps, each followed with a curing step. FIG. 7E illustrates a partially filled cavity preparation. The dentist continues to perform filling and curing steps until the filling material has taken the desired shape 22 (FIGS. 3-6). At this point, FIG. 7F, the band 10 now maintains a passive contact with the tooth 32 at the contact area 42. Also, the band 10 is bonded to the filling material and the tooth surfaces adjacent the cavity. Next, FIG. 7G, the excess, non-bonded portion of band 10 is cut away from the bonded portion of band 10. The cut edges 53 of the band 10 are then finished to form a smooth, polished surface.

As such, the problem of "open contacts" caused by removal of conventional matrix bands is obviated in the present invention because band 10, which was initially placed in a position to close the "open contact" before filling, is not removed and remains in place as an integral part of the restoration. Also, since no wedge has been used, the teeth 30, 32 will not move with respect to each other after band placement.

An alternative method of using band 10 to restore tooth 30 is also contemplated wherein fewer curing cycles are required. The tooth 30 is prepared to the condition shown in FIG. 7A. Then the margins 36, 37 and 44 plus the interior surface of cavity preparation 20 has a dental bonding agent spread thereon. Note that the band 10 has not been placed yet. The bonding agent is then cured. At this point, the band 10 is placed around the tooth 30 and held in place by the dentist in the position shown in FIG. 7C. Uncured composite resin is then condensed into the proximal portion of the cavity preparation 20. Once the uncured composite resin is placed, the band 10 is drawn tightly against the cervical margin 44. The more occlusal portion of the band 10 is angled to obtain passive contact with the area 42 of the adjacent tooth 32. This entire complex is then cured. This results in a bond between the tooth 32, the composite resin, and the band 10 in one curing cycle. The remainder of the cavity preparation 20 can now be filled and cured, after which the band 10 is trimmed and finished.

Figure 8:
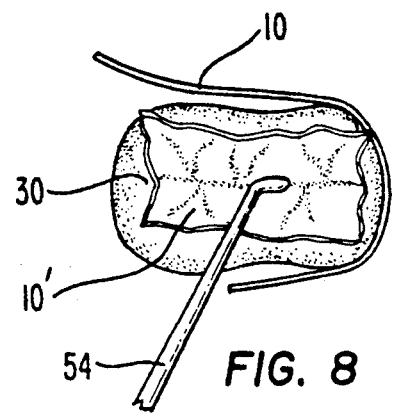
FIG. 8 is a top view similar to the view shown in FIG. 6 and FIG. 7D.

Once the band 10 is first bonded to the tooth 30, one of the free ends of band 10 can be cut away and used as a condensing aid to prevent the problems due to stickiness mentioned earlier. As seen in FIG. 8, a piece 10' has been cut from band 10 and is used to help condense the occlusal portion of the cavity preparation 20. This band piece 10' functions as a protective layer between the uncured composite resin and the metal condensing instrument 54. The FIG. 8 procedure solves the problem of stickiness; the uncured composite resin never touches the metal instrument 54. Using the band piece 10' and instrument 54, the dentist may remove gross excess amounts of composite resin from the margins of the cavity preparation 20 and may contour the occlusal portion of the filling prior to curing. As a result, trimming and finishing are greatly facilitated.

In cases in which an existing composite filling must be repaired, this invention provides an easy method for correction. The bondable band 10 is used as previously described. The difference is that uncured composite resin is placed against cured composite resin rather than into a cavity preparation.

In similar fashion, this band 10 can be used to repair ceramic and metal restorations with a composite resin. The difference between repair of a tooth with an existing composite resin versus a ceramic or metal restoration lies solely in choosing the appropriate etching and bonding agents which is within the skill of those skilled in these arts.

Figure 9:
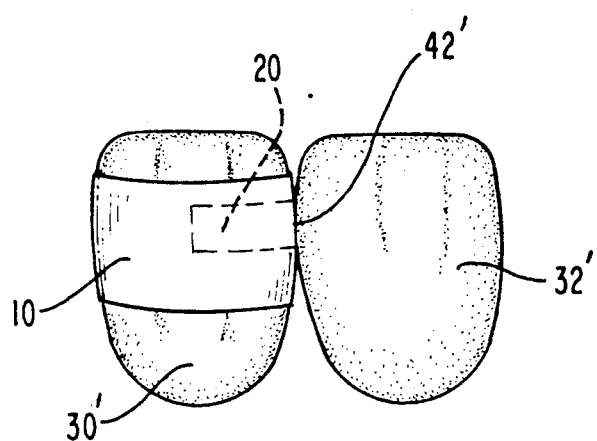
FIG. 9 is a diagrammatic elevation illustrating the structure of FIG. 1 in combination with a pair of anterior teeth.

FIG. 9 illustrates the use of band 10 in composite resin restorations of the class III type. In FIG. 9, the band 10 is used on anterior teeth 30', 32' with an interproximate cavity preparation 20. In this situation, the cavity preparation 20 is first prepared, the bonding liquid then applied, the cavity preparation 20 is next filled, the band 10 is now inserted and additional composite resin is applied, if necessary, to insure that the band 10 comes into passive contact with contact area 42'. Next the excessive, unbonded portion of band 10 are removed and the restoration is trimmed, polished and finished, as needed.

Cavities that extend deeply under the gingiva 60 (FIG. 10) are especially problematic to composite restorations. Conventional composite resins are very sensitive to moisture contamination. Moisture contamination will lead to filling failure because the contamination affects the integrity of the bond. Moisture control is difficult under ideal conditions and may be nearly impossible in deep subgingival cavity preparations. Although it is possible to successively use the band 10, in the procedures described above, the chances of bond failure, though small, are sufficiently large in some cases that an alternative two-step procedure is indicated.

Figure 10:
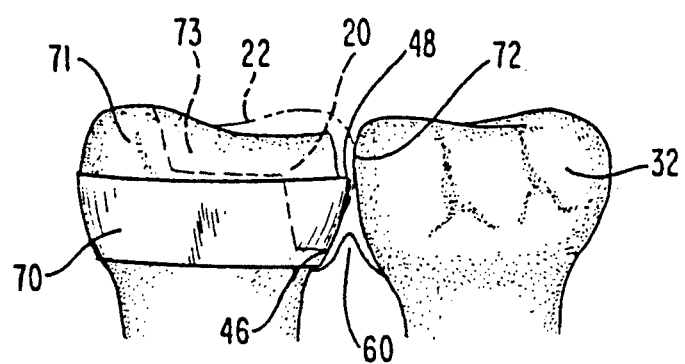
FIG. 10 is an elevation of a tooth having a cavity with a deep subgingival cervical margin illustrating its preparation for use with the structure shown in FIG. 1.

This method involves using a stainless steel matrix band 70 (FIG. 10). The band 70 is very tightly adapted to the tooth 71 with complete disregard to the contact area 72. The important region is the cervical margin 46. The band must be tight enough to prevent moisture seepage between the junction of the tooth 71 and the band 70 in the cervical margin 46. Once the band 70 is secured, the cavity preparation 73 is bonded and filled. The composite resin is built up to a height where the top of the composite resin forms and edge 48 that is higher than the level of the gingiva 60. Once this level is reached, the steel band 70 is removed. Now the remainder of the cavity preparation 73 is filled as indicated in the description of FIGS. 7A-7G. In this case, the top of the composite resin serves as the floor and the top edge 48 thereof serves as the cervical margin 44.

Unlike conventional banding methods, a wedge is not required when using this invention. Thus, the problems associated with use of a wedge are avoided. These problems are pain on insertion, trauma to the interdental papilla, bleeding, deformation of the matrix band, and excessive separation of adjacent teeth.

This invention and methods for its use as previously described have many advantages over the use of prior art matrix bands. First, use of the band 10 solves the problem of "open contacts" in cavity classes II, III, and IV restorations. Second, use of the band 10 provides an improved method for contouring composite restorations in cavity class I, II, III, and IV. Third, use of the band 10 facilitates the condensation of uncured composite resins in all cavity classes I through V. Fourth, use of the band 10 facilitates the process of trimming and finishing the composite restoration. Fifth, use of the band 10 facilitates repairs to composites, ceramics, and metals using bondable resins. Sixth, the band 10 can be used in multistep procedures using conventional bands for the first step and the band 10 at a later stage (FIG. 10). Seventh, the band 10 can be used by dentists without extensive training. It is similar enough in use to current techniques that it can be easily incorporated into contemporary dental practice. Eighth, the band 10 may be made in only one size. Multiple sized and shaped bands are usually unnecessary and unwarranted. Ninth, a wedge is not needed and most problems associated with the use of a wedge are avoided. It is noted also that since the band 10 has free ends, it is possible that it can be combined with existing matrix band holders.

While the invention has been described with reference to the preferred embodiment thereof, it will be appreciated by those of ordinary skill in the art that modifications can be made to the structure and elements of the invention without departing from the spirit and scope of the invention as a whole.

I claim:

1. A matrix band for use in composite restoration of a tooth, said matrix band being formed as a thin, elongated, flexible strip of material bondable to said tooth and said composite, wherein said band is formed of a mixture of light-activated material and a liquid resin.

2. The matrix band of claim 1 wherein said light-activated material is fluoroaluminosilicate glass powder.

3. The matrix band of claim 2 wherein said liquid resin is BIS-GMA.

4. The matrix band of claim 3 wherein the weight-ratio of said powder to said resin falls in the range of 3.3:1 and 0.5:1.

5. The matrix band of claim 3 wherein the weight-ratio of said powder to said resin is substantially 1.6:1.

6. A method for composite restoration of a tooth having a cavity comprising the steps of:
   forming a prepared cavity in said tooth;
   inserting a thin, flexible composite matrix band between said tooth and an adjacent tooth;
   holding said band firmly against said tooth with the surface of said band passively abutting said adjacent tooth;
   applying a bonding agent to the surface of said prepared cavity, to said band adjacent said cavity and to regions of contact between said band and said cavity;
   curing said agent;
   filling said prepared cavity with a composite resin;
   curing said resin; and
   removing unbonded portions of said band.

7. The method of claim 6 further including removing an unbonded portion of said band and placing it over said composite resin, and using a rigid instrument to push against said portion of said band to condense said resin.

8. A method for composite restoration of a tooth having a cavity comprising the steps of:
   forming a prepared cavity with margins including a cervical margin in said tooth;
   applying a bonding agent to said margins and the surface of said prepared cavity;
   inserting a thin, flexible composite matrix band between said tooth and an adjacent tooth;
   holding said band firmly against said tooth with the surface of said band passively abutting said adjacent tooth;
   filling a portion of said prepared cavity with a composite resin;
   curing said resin and said agent to bond a portion of said band to said resin;
   filling the remainder of said cavity with said resin;
   curing the resin; and
   removing unbonded portions of said band.

9. A method for composite restoration of a tooth having a cavity comprising the steps of:
   forming a prepared cavity with margins including a cervical margin in said tooth;
   applying a bonding agent to said margins and the surface of said prepared cavity;
   inserting a thin, flexible composite matrix band between said tooth and an adjacent tooth;
   holding said band firmly against said tooth with the surface of said band passively abutting said adjacent tooth;
   filling a portion of said prepared cavity with a composite resin;
   curing said resin and said agent;
   filling the remainder of said cavity with said resin;
   curing said resin;
   removing unbonded portions of said band; and
   placing a portion of said unbonded portion of said band over said composite resin, and using a rigid instrument to push against said portion of said band to condense said resin.

10. A method for composite restoration of a tooth having a cavity with a deep subgingival cervical margin comprising the steps of:
   partially restoring said tooth to fill a portion of said cavity to produce a restored, supergingival cervical margin;
   inserting a thin, flexible composite matrix band between said partially restored tooth and an adjacent tooth;
   holding said band firmly against said tooth with the surface of said band passively abutting said adjacent tooth;
   applying a bonding agent to the surface of said cavity, to said band adjacent said cavity and to regions of contact between said band and said cavity;
   curing said agent;
   filling said cavity with a composite resin;
   curing said resin; and
   removing unbonded portions of said band.

* * * * *

UNITED STATES PATENT AND TRADEMARK OFFICE
CERTIFICATE OF CORRECTION

PATENT NO. : 5,035,615
DATED : July 30, 1991
INVENTOR(S) : Franklin Din

It is certified that error appears in the above-identified patent and that said Letters Patent is hereby corrected as shown below:

Column 7, line 3, please delete "and" and insert instead the word --an--.

Signed and Sealed this

Twelfth Day of January, 1993

Attest:

DOUGLAS B. COMER

*Attesting Officer*    Acting Commissioner of Patents and Trademarks